United States Patent [19]

Renard

[11] Patent Number: 5,112,753

[45] Date of Patent: May 12, 1992

[54] METHOD OF IDENTIFICATION AND PREPARATION OF PROBES FOR PESTIVIRUSES, OLIGONUCLEOTIDES AND PROBES THUS OBTAINED AND A METHOD OF DETECTION OF PESTIVIRUSES

[75] Inventor: André J. J. Renard, Didier G. J. Allaer, Michel T. J. Rossius, Dolores Vaira, all of Liege, Belgium

[73] Assignees: Societe Europeene De Biotechnologie, Esneux, Belgium; Rhone Merieux, Lyon, France

[21] Appl. No.: 536,892

[22] Filed: Jun. 12, 1990

[30] Foreign Application Priority Data

Jun. 15, 1989 [FR] France .................. 89 07970

[51] Int. Cl.$^5$ .................. C12Q 1/70; C12Q 1/68; C12P 19/34; C07H 15/12
[52] U.S. Cl. .................. 435/5; 435/6; 435/91; 536/26; 536/27; 536/28; 536/29; 935/77; 935/78; 436/94; 436/501
[58] Field of Search .................. 435/5, 6, 91; 536/26, 536/27, 28, 29; 935/77, 78

[56] References Cited

PUBLICATIONS

Collett et al., Virology 165: 191–199 (1988).
Saiki et al., Science 230: 1350–1354 (Dec. 1985).
Urdea, Gene 61: 253–264 (1987).

*Primary Examiner*—Robert A. Wax
*Assistant Examiner*—Stephanie W. Zitomer
*Attorney, Agent, or Firm*—Larson and Taylor

[57] ABSTRACT

In the method of identification and preparation of general and/or specific probes for varieties of Pestivirus, a length of approximately 110 to 115 bases, towards the 5' end on the Pestivirus genome in the non-coding region corresponding to the region situated between bases 200 and 310 of the genome of the BVD Osloss virus, is amplified by means of converging primers in a polymerase chain reactions, the amplified length is sequenced and, by comparison with similar previously sequenced lengths of other varieties of Pestivirus, the homologous and/or specific oligonucleotidic sequences of the probes are identified.

33 Claims, 2 Drawing Sheets

FIG. 1 (sheets 1 and 2)

```
                                      1                                                          44      51       60
         A    Ppcal9.Frg    aagaCAcaccTTAa..CCt.aGCgGGGGTcGctagGg..tgAAAtca......caccacgtGa
Hog      B    Ppccogla.Frg  aagaCAcaccTTAa..CCt.aGCgGGGGTcGctagGg..tgAAAtca......caccacgtGa
cholera  C    Ppcc30.Frg    aagaCAcaccTTAa..CCt.aGCgGGGGTcGctagGgatGgAAAtca......caccacgtGa
         D    Ppcppl.Frg    aagaCAcaccTTAa..CCt.aGCgGGGGTcGctagGgg.gAAAtca......caccacgtGa
         E    Bdav.Frg      atgaCAcgctTTAggCC...gGCaGGGGTcGcc.gGgtcgAAAaca..cctcactg..tGt
BORDER   F    Bdbdnc.Frg    aagaCAtgctTTAatCCt.gGCgGGGGTcGccagGg..tgAAAaca..cctaatgg..tGt
         G    Bdbdc.Frg     aagaCAtgctTTAatCCt.gGCgGGGGTcGccagGg..tgAAAaca..cctaatgg..tGt
         H    Bvdsgnc.Frg   aaagCAcatcTTAa..CCtgaGcgGGGGTcGcccaGg..taAAAgcagttctaaccgactGt
         I    Bvdlamc.Frg   acagCAcatcTTAa..CCtgaGCgGGGGTcGctcaGg..cgAAAacggt.ctaaccgaccGc
         J    Bvdmd1.Frg    aaagCAcatcTTAa..CC..gaGCgGGGGTcGctcGa..caAAAacagt.ttgatcaactGc
         K    Bvdnad1.Frg   aaagCAcatcTTAa..CCtgaGCgGGGGTcGcccaGg..taAAAgcagtttaaccgactGt
         L    Bvdny.Frg     acagCAcatcTTAa..CCtgaGCgGGGGTcGttcaGG..tgAAAacggt.ttaaccaaccGc
BVD      M    Bvdosnc.Frg   acagCAcatcTTAa..CCtgaGCgGGGGTcGttcaGg..tgAAAgcggt.ttaaccaaccGc
         N    Bvdosc.Frg    acagCAcatcTTAa..CCtgaGCgGGGGTcGctcaGg..tgAAAgcggt.ttaaccaaccGc
         O    Vp123.Frg     acagCAcatcTTAa..CCtgaGCgGGGGTcGctcaGg..cgAAAacggt.ttgaccaaccGc
         P    Ve48nc.Frg    acagCAcatcTTAa..CCtggGCgGGGGTcGttcaGg..tgAAAacggt.ttaaccaaccGc
         Q    88753.Frg     acagCAcatcTTAg..CCtgaGCgGGGGTcGcccaGg..tgAAAgcggtgaagacagaccGc
         R    Sgclncl.Frg   acggCAcatcTTAa..CCtatGCgGGGGTtGcatgGg..tgAAA..ggcccattcgtggcGt
         S    Sgclnc2.Frg   tcggCAcatcTTAa..CCtatGCgGGGGTtGcatgGg..tgAAAgc.cattcgtggcGt
              Consensus     *-----CA-----TTA--CC---GC-GGGGT-G----G----AAA--------G-
```

* Consensus = a sequence common to all the genomes.

FIG. 1 (sheet 2)

| | 61 68 72 93 119 |
|---|---|
| Ppca19.Frg | TggGagtACgaCCTGATAGGGtGctGCAGAGgCCcaC..tattaggctagTA.tAAaaa |
| Ppccogla.Frg | TggGagtACgaCCTGATAGGGtGctGCAGAGgCCcaC..tattaggctagTA.tAAaaa |
| Ppcc30.Frg | TggGagtACgaCCTGATAGGGtGctGCAGAGgCCcaC..tattaggctagTA.tAAaaa |
| Ppcppl.Frg | TggGagtACgaCCTGATAGGGtGctGCAGAGgCCcaC..tattaggctagTA.aAAaaa |
| Bdav.Frg | TggGgttACagCCTGATAGGGtGctGCAGAGgCCcaC.gcat.aagctagTA.tAAaaa |
| Bdbdnc.Frg | TggGgttACagCCTGATAGGGtGctGCAGAGgCCcaC.gtat.aggctagTA.tAAaaa |
| Bdbdc.Frg | TggGgttACagCCTGATAGGGtGctGCAGAGgCCcaC.gtat.aggctagTAtaAAaaa |
| Bvdsgnc.Frg | TacGaatACagCCTGATAGGGtGctGCAGAGgCCcaCtgtt.....ctgcTActAAaaa |
| Bvdlamc.Frg | TacGaatACagCCTGATAGGGcGctGCAGAGgCCcaCtgta.....ttgcTActAAaaa |
| Bvdmdl.Frg | TacGaatACagCCTGATAGGGtGctGCAGAGgCCcaCtgta.....ttgcTActAAaaa |
| Bvdnadl.Frg | TacGaatACagCCTGATAGGGtGctGCAGAGgCCcaCtgta.....ttgcTActAAaaa |
| Bvdny.Frg | TacGaatACagCCTGATAGGGtGctGCAGAGgCCcaCtgta.....ttgcTActAAaaa |
| Bvdosnc.Frg | TacGaatACagCCTGATAGGGtGctGCAGAGgCCcaCtgta.....ctgcTActAAaaa |
| Bvdosc.Frg | TacGaatACagCCTGATAGGGtGctGCAGAGgCCcaCtgta.....ttgcTActAAaaa |
| Vp123.Frg | TacGaatACagCCTGATAGGGtGctGCAGAGgCCcaCtgta.....ttgcTActAAaaa |
| Ve48nc.Frg | TacGaatACagCCTGATAGGGtGctGCAGAGgCCcaCtgta.....ttgcTActAAaaa |
| 88753.Frg | TacGaatACagCCTGATAGGGtGctGCAGAGgCCcaCtgta.....atgcTActAAaaa |
| Sgcincl.Frg | TatGgacACagCCTGATAGGGtGtaGCAGAGaCCtgC..tatt...ccgcTAgtAAaa. |
| Sgcinc2.Frg | TatGgacACagCCTGATAGGGtGtaGCAGAGaCCtgC..tatt...ccgcTAgtAA... |
| Consensus | T--G---AC--CCTGATAGGG-G--GCAGAG-CC--C-------------TA--AA--- |

METHOD OF IDENTIFICATION AND PREPARATION OF PROBES FOR PESTIVIRUSES, OLIGONUCLEOTIDES AND PROBES THUS OBTAINED AND A METHOD OF DETECTION OF PESTIVIRUSES

The invention relates to a method of identification and of preparation of general and specific probes for varieties of Pestivirus, to new oligonucleotides intended in particular to form probes for the detection of viruses of the genus Pestivirus by DNA-RNA or DNA-DNA in vitro molecular hybridization, to the probes obtained as well as methods of detection utilizing the said probes according to the invention.

In the present classification, the genus Pestivirus comprises essentially three species, i.e. bovine diarrhoea virus (BVD), the hog cholera virus and Border disease virus. These different species are themselves divided into numerous varieties or sub-species, of which very few are known in any precise manner.

The viral infections caused by these different viruses display symptoms which are often difficult to distinguish from those accompanying other animal viral diseases, which renders diagnosis difficult.

Furthermore, the risks of serum contamination render indispensible the detection of Pestiviruses in serum used in the preparation of animal products, vaccines, etc.

Nevertheless, diagnostic techniques and traditional detection techniques, ELISA for example, sometimes prove insufficient.

The technique of molecular hybridization, in which a labelled sequence of DNA or RNA (a probe) is used to detect homologous or complementary sequences, has been known for a long time.

In the present case, the difficulty arises in particular from the great diversity of variants or sub-species since it is essential to arrive at a means of detection and eventual identification for most, and if possible, for all the Pestiviruses.

The object of the invention is thus to provide a method of identification and of preparation of general and specific probes for all Pestiviruses.

Another objective of the invention is to provide oligonucleotides of complementary sequence to the sequences common to all the Pestiviruses and of sequences specific to each species and sub-species, capable of being used as or incorporated into molecular hybridization probes, or mixtures of such probes intended for the detection and the identification of viruses of the Pestivirus genus.

A further objective of the invention is to provide a method of detection and identification of Pestiviruses in a sample, that is simple, easy to carry out, rapid and dependable and that is capable of being at least partly automated.

The applicant has discovered that it is particularly valuable to sequence a length of the genome of various Pestivirus varieties the length being located in the same region on the genome, i.e. on the 5' end in the non-coding region and more precisely a length of about 110 bases corresponding to the region situated between base 200 and base 310 of the genome of BVD Oslos.

The applicant has in particular sequenced this length (110 bases) in the genome of 19 varieties of Pestivirus (see their origin and their biotype in table 1):
12 varieties of the BVD virus
3 varieties of the Border disease virus and
4 varieties of the Hog cholera virus,
it being understood that the complete sequences of two varieties of BVD virus are already known (BVD Osloss C variety: EP-A-0.208.672 and BVD Nadl, Collet et al., Virology, 165, 1988, p. 191-199).

A comparative study of these sequences has allowed determination of a sequence of 20 bases (bases 93 to 72 in FIG. 1) more or less common to all Pestiviruses and, likewise, sequences specific to each species and sub-species.

The invention relates to a method of identification and of preparation of general and specific probes of varieties of Pestivirus, characterized in that a length of about 110 to 115 bases, situated towards the 5' end of the Pestiviruses genome in the non-coding region corresponding to the region situated between bases 200 and 310 of the genome of BVD Osloss virus, is amplified by means of convergent primers in a polymerase chain reaction according to SAIKI et al, Science 230, 1530-1534 (1985), that the amplified length is sequenced and that, by comparison with similar previously sequenced lengths of other varieties of Pestivirus, the homologous and/or specific oligonucleotide sequences are identified and that the said sequences are used for the production of probes.

Preferably, the amplification is carried out by means of two primers or amplimeres having respectively the following sequences:

| |
| --- |
| 5' ACG TGG ACG AGG GCA TGC CC 3' |
| 5' TGT GCC ATG TAC AGC AGC GA 3'. |

This length of about 110 to 115 bases may also be defined by the fact that the zone of hybridization of the second primer is situated just before the AUG initiation codon in the first reading frame of the Pestivirus genome.

Preferably, a specific sequence is sought outside the portion extending about between bases 72 and 93 of the amplified zone.

Preferably, a general sequence is sought in the portion extending about between bases 72 and 93 of the amplified zone.

Preferably, general and/or specific sequences are sought in the sequences of several or all of the viruses referenced A to S in FIG. 1.

BRIEF DESCRIPTION OF THE DRAWINGS

FIG. 1 shows the DNA translation of the genome sequences of the Pestiviruses A to S which are listed in Table 1 below. The sequences correspond to a same region of 119 bases of the genome of BVD Osloss, including the region of about 110 to 115 bases according to the invention (1-110 or 115 on FIG. 1). Sequence parts common to all Pestiviruses are represented with capital letters and the other parts with small letters.

The invention also relates to oligonucleotides obtained by the method described above.

The invention also relates to oligonucleotides whose sequence is complementary to the general sequences and oligonucleotides whose sequence is complementary to the specific sequences, of the different genomes of the 19 varieties of Pestivirus mentioned above.

The oligonucleotides of the invention comprise the following sequences:

Oligonucleotide 1 complementary to bases 93 to 72 of all the Pestiviruses of FIG. 1 except varieties I, R and S:

5' GTG GGC CTC TGC AGC ACC CTA TCA GG 3'.

Oligonucleotide 2 complementary to bases 93 to 72 of variety I:

5' GTG GGC CTC TGC AGC GCC CTA TCA GG 3'.

Oligonucleotide 3 complementary to bases 93 to 68 of varieties R and S:

5' GCA GGT CTC TGC TAC ACC CTA TCA GGC TGT 3'.

Oligonucleotide 4 complementary to bases 68 to 44 of varieties of the Hog cholera virus:

5' ACT CCC ATC ACG TGG TGT GA 3'.

Oligonucleotide 5 complementary to bases 68 to 44 of the Border E variety:

5' AAC CCC AAC ACA GTG AGG TGT 3'.

Oligonucleotide 6 complementary to bases 68 to 44 of the Border F and G varieties:

5' AAC CCC AAC ACC ATT AGG TGT 3'.

Oligonucleotide 7 complementary to bases 69 to 51 of the BVD H and K varieties:

5' TAT TCG TAA CAG TCG GTT A 3'.

Oligonucleotide 8 complementary to bases 69 to 51 of the BVD L, M, N, and P varieties:

5' TAT TCG TAG CGG TTG GTT A 3'.

Oligonucleotide 9 complementary to bases 69 to 51 of the BVD O variety:

5' TAT TCG TAG CGG TTG GTC A 3'.

Oligonucleotide 10 complementary to the bases 69 to 51 of the BVD I variety:

5' TAT TCG TAG CGG TCG GTT A 3'.

Oligonucleotide 11 complementary to bases 69 to 51 of the BVD J variety:

5' TAT TCG TAG CAG TTG ATC A 3'.

Oligonucleotide 12 complementary to bases 69 to 51 of the BVD Q variety:

5' TAT TCG TAG CGG TCT GTC T 3'.

It is, of course, possible to replace certain nucleotides by elements comprising equivalent bases, for example inosine, and these constructions are by simple equivalance within the scope of the invention.

Preferably, the oligonucleotides comprise at least 10 and preferably at least 15 to 17 consecutive bases of the corresponding sequence.

The invention furthermore has for its object probes produced by the method of identification and preparation of probes according to the invention.

The invention also relates to general and specific nucleic acid probes comprising respectively all or part of the said general and specific sequences described above.

For reasons of selectivity of hybridization, the said nucleic acid probes, in preference, comprise a minimum of 15 to 17 consecutive bases of the corresponding oligonucleotide sequence. Advantageously they comprise the totality of the said sequence.

However, in certain cases, the utilisable probes may comprise a lesser number of bases, for example 10 to 12.

For their detection, the nucleic acid probes according to the invention may be labelled according to any known technique. They may for example be coupled with radioisotopes.

For detection by non-radioactive means, the nucleic acid probes may comprise additional groups, such as amine groups, SH or any other molecule allowing coupling of a non-radioactive label.

It may also be envisaged, in a known manner, to graft onto the nucleotides identical known sequences onto which a nucleic fragment detectible by all the probes will couple, for example a nucleic acid fragment coupled to a radioisotope.

Preferably, the probes according to the invention will be produced by chemical synthesis, for example by the method of "Phosphoroamidites" (Beaucage, S. L., and Caruthers, M. H. (1981), Tetrahedron Lett. 22, 1859), or by any other appropriate method.

For detecting Pestiviruses by a probe, a mixture may advantageously be used containing the probe corresponding to oligonucleotide 1 and a probe corresponding to one of the nucleotides 2 and 3 or, preferably, a mixture of these three probes.

The detection of the Hog Cholera virus may be carried out with the probe corresponding to oligonucleotide 4; that of Border Disease with a mixture of probes corresponding to oligonucleotides 5 and 6; and that of BVD with a mixture of probes corresponding to oligonucleotides 7 to 12. Any combinations are of course possible.

According to the invention, molecular hybridization by means of the probes according to the invention may either be carried out on a liquid sample, for example the animal's blood or serum, for example by means of the method of Mickey S. Urdea., (1987) Gene 61, 253–264, or on a sample containing the total cellular RNA of the animal.

According to the invention, a preliminary amplification of the RNA so as to increase the sensitivity of the detection could also be carried out according to (SAIKI et al., Science 230, 1350–1354 (1985)).

The invention also relates to primers comprising respectively the following sequences:

5' ACG TGG ACG AGG GCA TGC CC 3'
5' TGT GCC ATG TAC AGC AGA GA 3' which are particularly intended for carrying out the method of identification and preparation of probes and for the amplification stage of the method of detecting Pestivirus.

Other characteristics and advantages of the invention will appear on reading the following description, given by way of non-limiting example and with reference to FIG. 1 which shows the DNA transcription of the Pestivirus genome sequences according to the invention.

I—DETECTION IN ANIMAL SERUM

The process described by Mickey S., Urdea et al. in Gene, 61 (1987) 253–264 may be followed.

The following procedure may also be used.

The nucleic acids are extracted from the serum as described by D. Larzul et al (D. Larzul et al, Journal of Hepatology, 1987; 5/199–204)

the serum is incubated for one hour at 70° C. in a solution:

25 mM sodium acetate pH=6.5
2.5 mM EDTA
0.5% SDS (may be replaced by Nonidet P40 (Sigma))
12.5 μg/ml salmon sperm DNA (see preparation below)
2.5 mg/ml Proteinase K (Boehringer, Mannheim)

Add a volume of phenol (see preparation in point II-1), agitate in a vortex, centrifuge for 3 minutes at 8000 g, then recover the upper phase.

Add a volume of diethyl ether, agitate in a vortex, pour off the upper phase, incubate for 30 minutes at 68° C. to eliminate traces of diethyl ether.

Add sodium acetate (final concentration 0.25M) and 2.5 volumes of ethanol. Leave to rest for at least 20 minutes at −70° C.

centrifuge for 15 minutes at 8000 g, pour off the supernatant, dry the residue and resuspend in a minimal volume of water.

carry out the amplification according to point III below.

carry out the detection by means of the detection process described by D. Larzul et al.

II DETECTION IN ANIMAL TOTAL CELLULAR RNA

1—Preparation of Cellular RNA

The preparation of cellular RNA is derived from the method described by Chomczinski, P. and Sacchi, N., Anal. Biochem, 162: 156–159 (1987).

a) Solutions

Denaturising solution: 4M guanidine thiocyanate, 25 mM sodium citrate, 0.5% sarcosyl, 0.1M 2-mercaptoethanol.

This solution will keep for 1 month at room temperature and the same solution without 2-mercaptoethanol keeps under the same conditions for 3 months.

2M Sodium acetate, pH=4.

Phenol: distilled phenol (kept in aliquots at −20° C.) equilibrated shortly before use with a solution of 50 mM Tris-HCl (pH 7.5), 5 mM EDTA (pH=7.5) (use a decanting flask; several equilibrations are necessary). The final solution keeps for 2 to 3 weeks at 4° C.

Chloroform/isoamyl alcohol (49:1 by volume).
Isopropanol.
Absolute Ethanol.
10% Sarcosyl.
PBS: 27mM KCl, 15 mM $KH_2PO_4$, 32 mM $Na_2HPO_4$, 137 mM NaCl.

b) Procedure

1. The volumes given in this procedure are calculated for the preparation of RNA from a cell monolayer of 80 $cm^2$. These volumes will be proportionally adjusted for other cellular monolayer surfaces (excluding steps 2 to 10).

2. Aspirate the culture medium and rinse the monolayer with 5 ml of PBS. Aspirate the supernatant.

3. The cells are lysed by means of 5 ml of denaturizing solutions. The mixture is transferred to a sterile 15 ml tube (clean the bottom of the culture container well with the lysis solution, the solution is often very viscous at this stage).

4. To this solution is added, successively and with gentle agitation by inverting the tube after the addition of each reactant, 0.5 ml of 2M sodium acetate, 5 ml of phenol and 1 ml of chloroform/isoamyl alcohol.

5. Cool on ice for 15 minutes.

6. Centrifuge 20 minutes at 10,000 g and 4° C.

7. Recover the aqueous phase (upper phase) taking care not to include the lower phase and the interphase, in which the DNA and the proteins are to be found.

8. Add 1 volume of isopropanol, and leave for at least 1 hour at −20° C.

9. Centrifuge for 20 minutes at 10,000 g and at 4° C.

10. Pour off the supernatant and resuspend the RNA residue in 0.7 ml of the denaturizing solution. Transfer the lot to a sterile 1.5 ml tube.

11. Precipitate the RNA by means of one volume of isopropanol. Leave it to rest for at least one hour at −20° C.

12. Centrifuge in a bench centrifuge at 8000 g for 10 minutes at 4° C.

13. Pour off the supernatant, dry the residue under vacuum (Speed vac) and resuspend in 200 μl of sterile water. Sarcosyl (0.5%) may be added to aid suspension of the residue. If the residue remains difficult to resuspend, heat for 10 minutes at 65° C. and agitate in a vortex several times for 15 seconds each time. Repeat this treatment once if necessary.

14. Add 200 μl of phenol, agitate by inverting the tube, then add 20 μl of chloroform/isoamyl alcohol and agitate as before.

15. Centrifuge for 3 minutes in a bench centrifuge (8000 g, 4° C.) and recover the aqueous phase (upper phase). Add 1 volume of chloroform/isoamyl alcohol, agitate by inverting the tube and centrifuge as before.

16. Recover the new aqueous phase, add sodium acetate (final concentration 0.25M) and 2.5 volumes of ethanol. Leave it to rest for at least 20 minutes at −70° C.

17. Centrifuge for 15 minutes in a bench centrifuge, at 8000 g, and pour off the supernatant. Dry the residue under vacuum (speed vac) and resuspend in a minimum volume of sterile water.

18. Determine the quantity of RNA obtained by reading the optical density at 260 nm:

Concentration of RNA (in μg/ml)=OD 260 (1 cm)/0.024. Generally, 200 μg of RNA are obtained per confluent 80 $cm^2$ cell monolayer.

19. Adjust the RNA concentration to 3.3 μg/μl with sterile water.

2—Detection of Viral RNA

A—Fixation of RNA or Nitrocellulose (or any other appropriate support: nylon, etc)

a) Solutions:

SSC 20×: Dissolve 175.3 g of NaCl and 88.2 g of sodium citrate in 800 ml of $H_2O$. Adjust the pH to 7.0 with several drops of 10N NaOH. Adjust the volume to 1 liter.

Formaldehyde (37%) in solution.

b) Procedure

1. To 3 μl (10 μg) of the total cellular RNA, add 0.3 μl of formaldehyde at 37% and heat for 20 minutes at 60° C. Keep at 0° C. on ice.

2. Place a sheet of nitrocellulose in SSC 20× for 5 minutes and then leave the nitrocellulose to dry for 10 minutes at ambient temperature on filter paper.

3. Place 3.3 μl of the RNA solution on the nitrocellulose to treated (the spot should not exceed 1 cm$^2$ approx.).

4. Rinse the nitrocellulose for 2 minutes in a solution of SSC 6× and leave to dry at ambient temperature for 15 minutes.

5. Cure the nitrocellulose for two hours at 80° C. under vacuum. The RNA thus placed on the nitrocellulose is stable for several weeks at ambient temperature in a dessicator (between two sheets of Whatman 3 mm filter paper).

B—Hybridization a) Solutions

Prehybridization solution:

SSC 4× (see above), Denhart 6× (0.12% weight-/volume (w/v) Ficoll 400, 0.12% w/v of PVP (polyvinylpyrrolidone), 0.12% w/v of bovine serum albumen fraction V), 0.1% w/v sodium dodecyl sulfate, 300 μg/ml of denatured salmon sperm DNA (see point b here after)

Hybridization solution:

SSC 4×

Denhard 2× (0.04% w/v Ficoll 400, 0.04% w/v PVP, 0.04% w/v bovine serum albumen fraction V), 3% w/v sodium dodecyl sulfate, 10% w/v dextran sulfate (by dilution of a 50% solution prepared in advance)

200 μg/ml denatured salmon sperm DNA (see point b here after)

50 ng/ml of labelled probe, heated for 10 minutes at 100° C.

solution I: SSC 2×, 0.1% w/v sodium dodecyl sulfate.

solution J: SSC 0.25×, 0.1% w/v of sodium dodecyl sulfate

TE: 10 mM Tris-HCl, pH=7.5, 1 mM EDTA, pH=7.5.

b) Preparation of Salmon Sperm DNA

1. Dissolve overnight, at ambient temperature, 1 g of salmon sperm DNA in 100 ml of 0.4M NaOH.

2. Boil for 45 minutes.

3. Cool on ice and bring to pH 7 with glacial acetic acid.

4. Centrifuge at 4000 g for 10 minutes at ambient temperature. Recover the supernatant.

5. Add 2 volumes of absolute ethanol, leave it to rest for at least 60 minutes at −20° C. Discard the supernatant.

6. Centrifuge at 8000 g for 15 minutes at ambient temperature.

7. Dry the residue under vacuum.

8. Dissolve it in 50 ml of TE.

9. Determine the quantity of DNA by reading the optical density at 260 nm. Concentration of DNA (in μg/ml)=OD 260(1 cm)/0.02. Adjust the concentration to 10 mg/ml.

10. The salmon sperm DNA thus prepared keeps for several months at −20° C.

c) Procedure

1. Heat the nitrocellulose for at least 4 hours at 55° C. (see point B-d/here after), in 1 ml/cm$^2$ of the prehybridization solution.

It is better to separate the filters in plastic bags. Drive out the air bubbles well before heat sealing the said bags.

2. Empty the bag and add 0.5 ml/cm$^2$ hybridization solution. Heat for at least 12 hours at 55° C. (cf point B-d/).

3. Empty the bag, open it and wash the filter at ambient temperature 4 times for 5 minutes in solution I.

4. Wash the filter at ambient temperature 4 times for 5 minutes in solution J.

5. Wash the filter, at 45° C. (cf point B-d), 3 times for 15 minutes in the solution J.

6. Take a reading depending on the type of labelling of the probes.

d) Temperatures

The temperatures mentioned in the procedure (point B-c/) depend on the TM of the probe (TM=temperature for which 50% of the probe has passed from the hybridized form to the non hybridized form).

The effect of the basic composition on the TM is more significant when the probes have less than 50 bases (MEIN-KOTH, J. and WAHL, G., ANAL. BIOCHEM., 138, p 267-284, 1984). For oligonucleotide probes comprising as many as 20 bases, it is possible, when hybridization is carried out under standard conditions (NaCl 0.9M approx), to determine an approximate TM value using the following formula. (Wallace, R. B. et al., Nucl. Acids Res., 6, p. 3543-3656, 1979): TM (°C.)=4 (G+C)+2 (A+T) in which G,C, A and T correspond to the numbers of the corresponding bases (Guanidine, Cytosine, Adenine, Thymine) in the oligonucleotide.

In filter hybridization (that is to say hybridization with a sample of nucleic acid immobilized on a membrane) by means of oligonucleotide probes, it should be possible to use a temperature of 5° C. lower to perfectly hybridize the sequences. When short probes are used, for each non-hybridized pair of bases, a further reduction in temperature of 5° C. is necessary to conserve the stability of the hybridization.

3—Detection of the Amplified RNA

The total cellular RNA of the animal has undergone amplification according to the process described in point III which follows.

During this amplification, the RNA was transcribed into DNA, such that here it is a DNA-DNA hybridization for which the procedure only differs for the point II A-b/, which becomes:

Heat 10 μl of the amplification product to 95° C. for 5 minutes.

Place on ice.

Place a sheet of nitrocellulose for 5 minutes in SSC 20×, them leave the nitrocellulose to dry for 10 minutes at ambient temperature on filter paper.

Place the 10 μl amplification mix on the nitrocellulose thus treated, by means of a commercial "Dot Blotting" apparatus. Cure the nitrocellulose for 2 hours at 80° C. under vacuum.

III—AMPLIFICATION OF RNA

The amplification procedure allows the amplification of sequences of nucleic acid by hybridizing primers and by synthesising the complementary strand of the sequence from the primer in the presence of triphosphate nucleotides and DNA polymerase or other polymerizing enzymes, such that the extension product of the primer serves as a template for the synthesis of the sequence and so forth.

The amplification utilizes two primers, each of them hybridising on a specific site on the complementary strand of DNA.

Primer A: 5' ACG TGG ACG AGG GCA TGC CC 3' (complementary to base 234 to base 254 of the BVD Osloss genome), Primer B: 5' TGT GCC ATG TAC AGC AGA GA 3' (complementary to base 385 to base 365).

1—Hybridization of the Primer for Inverse Transcriptase (Primer B)

a sample of between 1 and 8 µl of the RNA solution is used (10 to 20 µg)

20 ng of the oligonucleotide acting as primer is added, it is brought to a final concentration of:
250 mM KCl
2.5 mM Tris-HCl pH=7
0.25 mM EDTA
in a final volume of 10 µl,
  it is heated for 15 minutes at 65° C. then
  60 minutes at ambient temperature (or a higher temperature).

This temperature is determined by the oligonucleotide sequence and by the salt concentration of the medium, in the present case 0.25M. Different methods exist for determination of this temperature:

MEINKOTH, J. and WAHL, G. Anal Biochem 138, 267–284, 1984,

WALLACE, R. B. et al., Nucl. Acids Res., 6, 3543–3656, 1979,

GOEDDEL, D. V. et al., Nature, 287, 411–416, 1980,

SUGGS, S. V. et al., Proc. Natl. Acad. Sci. USA, 78, 6613–6617, 1981,

SZOSTAK, J. W. et al., Methods Enzymol., 68, 419–428, 1979,

SUGGS, S. V. et al., ICN-UCLA Symp. Dev. Biol., 23, 683–693, 1981.

2—Synthesis of the DNA Strand by Inverse Transcriptase 20 units of inverse transcriptase M-MLV are added: clone M-MLV (Moloney Murine Leukemia Virus) of inverse transcriptase, from Bethesda Research Laboratories.

It is adjusted to a final concentration of
7 mM Tris-HCl pH 8.6
7 mM MgCl$_2$
3.5 mM DTT (Dithiothreitol)
60 µM dATP, dTTP, dGTP, dCTP
5 ng/µl of primer B
75 mM KCl
in a final volume of 33 µl;
  It is left to incubate for 15 minutes at 22° C., then 45 minutes at 35° C.

3—Amplification the solution is brought to a concentration of:
50 mM KCl
10 mM Tris-HCl pH=8.6
2.5 mM MgCl$_2$
200 µg/ml Gelatine
200 µM dNTP
10 ng/µl of primer A
10 ng/µl of primer B
in a final volume of 100 µl:
  4 units of TAQ (Thermus Aquaticus DNA polymerase from New England Biolabs, ref. KALEDIN, A. S. et al., Biokhimia 45 (4), 644–651, 1980) are added:
  it is heated for 360 seconds at 93° C.
  A) it is heated for 60 seconds at 93° C.;
  B) it is brought to 22° C. for 120 seconds or to a higher temperature, and/or for a longer time depending on the case;
  C) it is incubated for 90 seconds at 72° C.;
  steps A) to C) are repeated 4 times;
  The following temperature cycle is then repeated 25 to 30 times:
  D) 60 seconds at 93° C.;
  E) 90 seconds at 55° C.;
  F) 90 seconds at 72° C.

The amplification stage may advantageously be carried out in an apparatus such as that described in European Patent Application EP-A-0,236,069.

ANNEXE

| Ref. | Strain | Origin | Biotype |
|---|---|---|---|
| Hog chlorea | | | |
| A | A19 | Rhone Merieux 1965 | non cytopathic |
| B | Thiverval | Launais et al[4]. (1972) | non cytopathic |
| C | C30-chinese | Rhone Merieux 1970 | non cytopathic |
| D | Alfort | Aynaud (1968)[1] | non cytopathic |
| Border disease | | | |
| E | AV-Aveyron | Rhone Merieux 1984 | non cytopathic |
| G-F | BD (c/nc) | Moredun 1983 | cytopathic |
| BVD | | | |
| H | Singer (c/nc) | Mc. Clurkin & Coria (1978)[5] | cytopathic |
| I | Lamspringe | Liess (1967) | cytopathic |
| J | Oregon | Gillespie et al. (1960)[2] | cytopathic |
| K | NADL | Gutekunst[3] (1963) | cytopathic |
| L | New-York | ATCC | non cytopathic |
| M-N | Osloss (c/nc) | Liess | cytopathic |
| O to S | Soil strains | | |

[1]Aynaud, J. M., 1968. Study of the single cycle multiplication of a clone of classic hog cholera virus by means of immunofluorscene. Ann. Rech. Veter. 1:25–36.
[2]Gillespie, J H., Baker, J. A. and McEntee, K., 1960. A cytopathic stain of bovine diarrhoea virus. Cornell vet. 50: 73–79.
[3]Guterkunst, D. E. and Malmquist, W. A., 1963. Separation of a soluble antigen and infectious particles of Bovine Virus Diarrhoea virus and their relationship to Hog Cholera. Can. J. Comp. Med. and Vet. Sc. 27; No. 5.
[4]Launais, M., Aynaud, J. M. and Corthier, G., 1972. Swine fever virus: properties of a clone (Thiverval strain) isolated in cell culture at low temperature. Use in vaccination. Rev. Med. Veter. 123: 1537–1554.
[5]McClurkin, A. W. and Coria, M. F., 1978. Selected isolates of bovine viral diarrhoea (BVD) virus propagated on bovine turbinate cells; virus titre and soluble antigen production as factors in immunogenicity of killed BVD virus. Arch. Virol. 58: 119–128.

We claim:
1. Process of identification and preparation of general oligonucleotide probes and specific oligonucleotide probes for varieties of Pestivirus, comprising the steps of:

a) amplification of a length of approximately 110 to 115 bases, situated towards the 5' end of the Pestivirus genome in the non-coding region corresponding to the region situated between bases 200 and 310 of the genome of the BVD Osloss virus, by means of convergent primers in a polymerase chain reaction,
b) determination of the sequence of the amplified length,
c) identification of the homologous and specific oligonucleotide sequences by comparison to other similar previously sequenced lengths of other Pestivirus varieties,
d) using these homologous and specific sequences for the production of general and specific probes respectively.

2. A process according to claim 1 wherein two primers having respectively the following sequences are used:

5' ACG TGG ACG AGG GCA TGC CC 3'
   5' TGT GCC ATG TAC AGC AGA GA 3'.

3. A process according to either of claims 1 or 2, wherein a specific sequence is identified outside the portion extending between about bases 72 and 93 of the amplified length.

4. A process according to either of claims 1 or 2, wherein a general sequence is identified in the portion extending between about bases 72 and 93 of the amplified length.

5. A process according to claim 3, wherein the general and/or specific sequences are identified in the sequences of several or all of the viruses referenced A to S in FIG. 1.

6. Oligonucleotides obtained by the process according to claim 1.

7. An oligonucleotide comprising the following sequence:

5' GTG GGC CTC TGC AGC ACC CTA TCA GG 3'.

8. An oligonucleotide comprising the following sequence:

5' GTG GGC CTC TGC AGC GCC CTA TCA GG 3'.

9. An oligonucleotide comprising the following sequence:

5' GCA GGT CTC TGC TAC ACC CTA TCA GGC TGT 3'.

10. An oligonucleotide comprising the following sequence:

5' ACT CCC ATC ACG TGG TGT GA 3'.

11. An oligonucleotide comprising the following sequence:

5' AAC CCC AAC ACA GTG AGG TGT 3'.

12. An oligonucleotide comprising the following sequence:

5' AAC CCC AAC ACC ATT AGG TGT 3'.

13. An oligonucleotide comprising the following sequence:

5' TAT TCG TAA CAG TCG GTT A 3'.

14. An oligonucleotide comprising the following sequence:

5' TAT TCG TAG CGG TTG GTT A 3'.

15. An oligonucleotide comprising the following sequence:

5' TAT TCG TAG CGG TTG GTC A 3'.

16. An oligonucleotide comprising the following sequence:

5' TAT TCG TAG CGG TCG GTT A 3'.

17. An oligonucleotide comprising the following sequence:

5' TAT TCG TAG CAG TTG ATC A 3'.

18. An oligonucleotide comprising the following sequence:

5' TAT TCG TAG CGG TCT GTC T 3'.

19. An oligonucleotide according to any one of claims 7 to 18, comprising at least 10 consecutive bases of the corresponding sequence.

20. Oligonucleotide probes prepared by a process according to claim 1.

21. A DNA probe for the detection of Pestiviruses by molecular hybridization, comprising all or part of the sequence according to claim 7, 8, or 9.

22. A DNA probe for the detection of Hog Cholera virus by molecular hybridization, comprising all or part of the sequence according to claim 10.

23. A DNA probe for the detection of Border disease virus by molecular hybridization comprising all or part of the sequence according to claim 11 or 12.

24. A DNA probe for the detection of the BVD virus, characterised in that it comprises all or part of the sequence according to any one of claims 13 to 18.

25. A mixture comprising at least two types of DNA probe according to claim 21.

26. A mixture comprising the two DNA probes according to claim 23.

27. A mixture comprising at least two types of DNA probe according to claim 24.

28. A DNA probe according to claim 21, comprising at least 10 consecutive bases of the corresponding sequence.

29. A DNA probe according to claim 21, obtained by chemical synthesis.

30. A process for the detection of a virus of the Pestivirus genus by molecular hybridization, wherein the probe according to any one of claims 1, 2 to 5 or 21 or the mixture according to any one of claims 25 to 29 is used on a liquid sample of blood or serum from a test animal.

31. A process for the detection of a virus of the Pestivirus genus by molecular hybridization, wherein the probe according to any one of claims 1, 2 to 5 or 21 or the mixture according to any one of claims 25 to 29 is used on a sample containing the total cellular RNA of a test animal.

32. A process according to claim 30, wherein before hybridization amplification of the viral RNA is carried out using a pair of appropriate primers.

33. Primers in particular for carrying out the process according to claims 1 or 32, wherein they comprise respectively the following sequences:

5' ACG TGG ACG AGG GCA TGC CC 3'
5' TGT GCC ATG TAC AGC AGA GA 3'.

* * * * *